United States Patent [19]

Wiederhöft et al.

[11] Patent Number: 5,840,111
[45] Date of Patent: Nov. 24, 1998

[54] NANODISPERSE TITANIUM DIOXIDE, PROCESS FOR THE PRODUCTION THEREOF AND USE THEREOF

[75] Inventors: Gerhard Wiederhöft, Krefeld; Kai Bütje; Peter-Joachim Barenthien, both of Duisburg; Michael Bödiger, Dormagen; Heinrich Alberts, Odenthal, all of Germany

[73] Assignee: Bayer AG, Germany

[21] Appl. No.: 744,421

[22] Filed: Nov. 8, 1996

[30] Foreign Application Priority Data

Nov. 20, 1995 [DE] Germany .................. 195 43 204.5

[51] Int. Cl.⁶ ............................................. C09C 1/36
[52] U.S. Cl. ................. 106/436; 106/438; 106/439; 106/441; 106/442; 106/443; 106/444; 106/446; 106/447; 423/598; 423/610; 423/616; 252/309; 252/313.1; 424/59; 429/111; 428/403
[58] Field of Search ................... 106/436, 441, 106/499, 438, 439, 442, 443, 444, 446, 447; 501/12, 134; 423/608, 610, 616, 598; 424/59; 428/403, 404; 252/309, 313.1; 210/348; 429/111

[56] References Cited

U.S. PATENT DOCUMENTS

| | | |
|---|---|---|
| 2,448,683 | 9/1948 | Peterson . |
| 4,842,832 | 6/1989 | Inoue et al. . |
| 5,028,417 | 7/1991 | Bhat et al. . |
| 5,049,309 | 9/1991 | Sakamoto et al. . |
| 5,215,580 | 6/1993 | Elfenthal et al. ............ 106/441 |
| 5,389,361 | 2/1995 | Osterried et al. . |
| 5,403,513 | 4/1995 | Sato et al. ............... 252/309 |
| 5,443,811 | 8/1995 | Karvinen . |
| 5,449,607 | 9/1995 | Wilton . |
| 5,468,463 | 11/1995 | Butje et al. . |
| 5,536,448 | 7/1996 | Takahashi et al. ............ 106/441 |
| 5,593,781 | 1/1997 | Nass et al. ................ 501/12 |

FOREIGN PATENT DOCUMENTS

| | | |
|---|---|---|
| 0261560 | 3/1988 | European Pat. Off. . |
| 0499863 | 8/1992 | European Pat. Off. . |
| 0505022 | 9/1992 | European Pat. Off. . |
| 2677012 | 12/1992 | France . |
| 2205288 | 12/1988 | United Kingdom . |
| 93/20569 | 10/1993 | WIPO . |

OTHER PUBLICATIONS

Patent Abstracts Of Japan, vol. 014, No. 470, Oct. 15, 1990 and JP 02194063, Jul. 31, 1990.
Patent Abstracts of Japan, vol. 012, No. 110, Apr. 8, 1988 and JP 62235215, Oct. 15, 1987.
Derwent Publication Ltd., London, GB; Class A35, and JP 60017190, Jan. 29, 1985.
Hydrothermal Preparation of Uniform Nanosize Rutile and Anatase Particles, pp. 663–671; Cheng et al; Jan. 31, 1995.
A General Nonhydrolytic Sol–Gel Route to Oxides; pp. 43–54; Sylvie Acosta et al; 1994. (no month).
Materials Science Forum vols. 152–53; pp. 43–54; J. Livage; The Sol–Gel Route to Advanced Materials; 1994. (no month).
Journal; pp. 1587–1595; Alkoxide–Derived Titania Particles: Use of Electrolytes to Control Size and Agglomeration Levels; Look et al; 1992. (no month).
Langmuir; pp. 1684–1689; Sol–Gel Serived $TiO_2$ Microemulsion Gels and Coatings; Papoutsi et al; 1994. (no month).

*Primary Examiner*—Michael Marcheschi
*Attorney, Agent, or Firm*—Connolly & Hutz

[57] ABSTRACT

The present invention relates to nanodisperse titanium dioxide, to a process for the production thereof and to the use thereof.

25 Claims, 2 Drawing Sheets

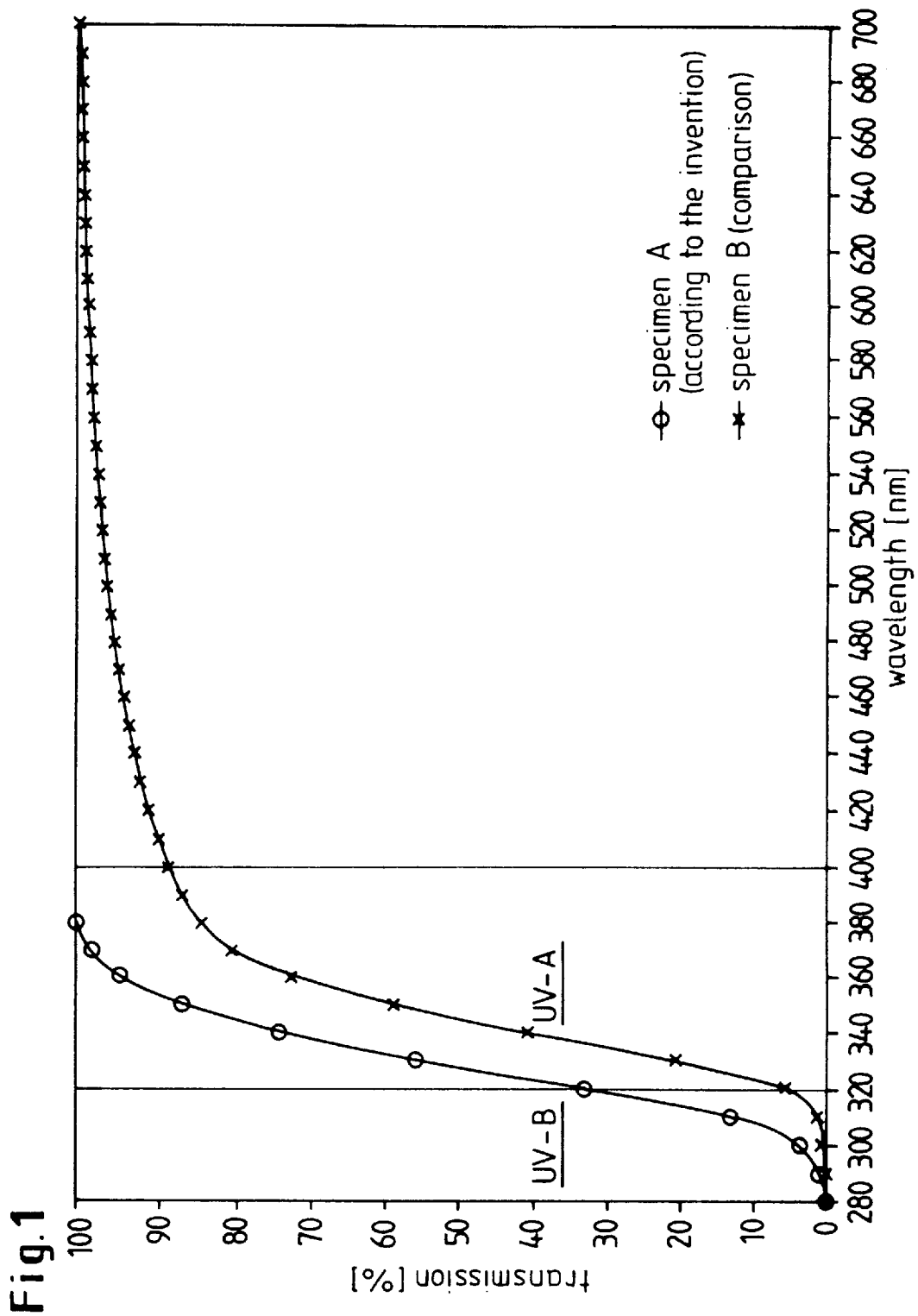

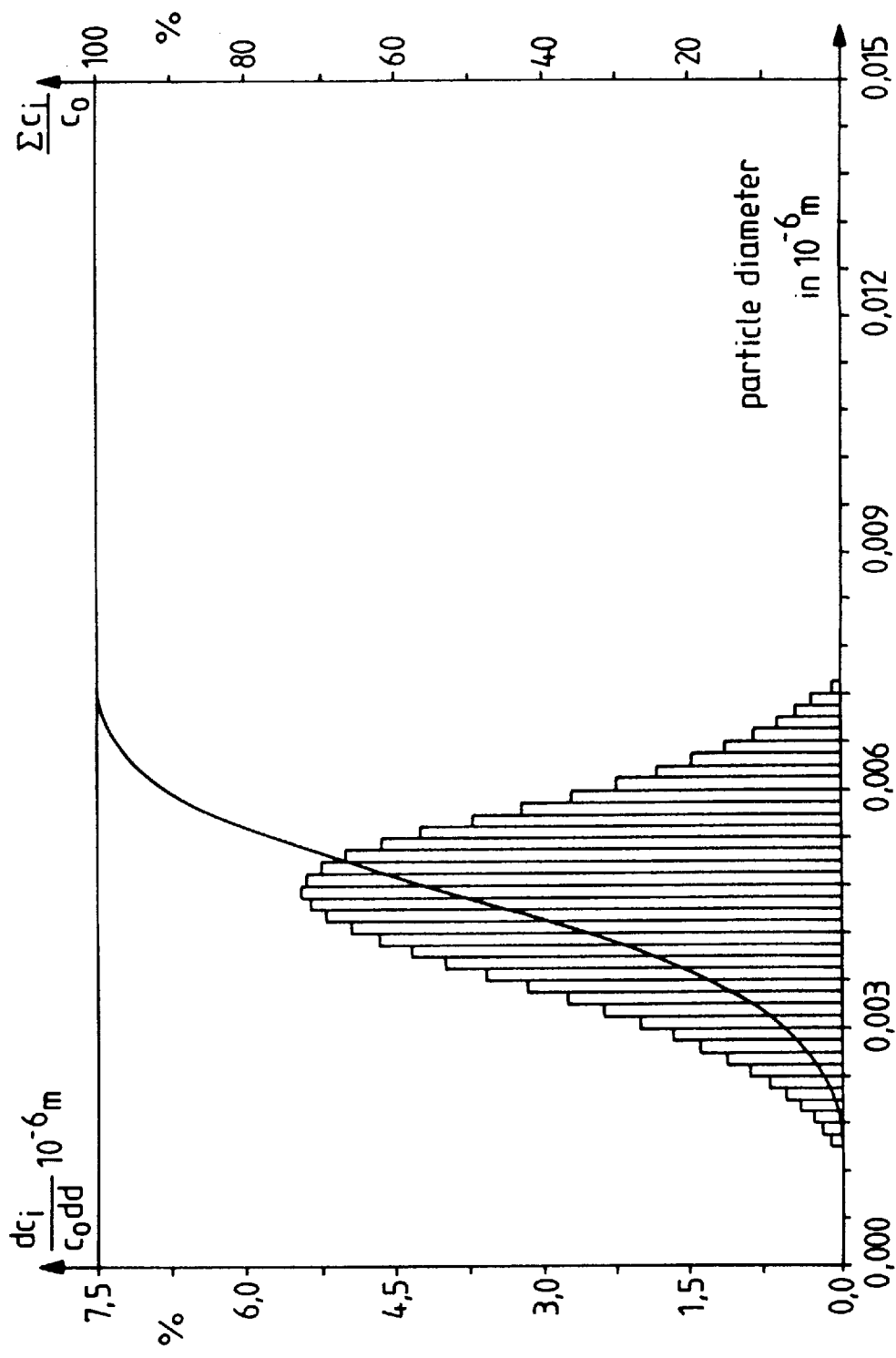
Fig. 2 Differential and integral particle size distribution

NANODISPERSE TITANIUM DIOXIDE, PROCESS FOR THE PRODUCTION THEREOF AND USE THEREOF

The present invention relates to nanodisperse titanium dioxide, to a process for the production thereof and to the use thereof.

For the purposes of the present invention, nanodisperse titanium dioxide ("nano-$TiO_2$") is taken to be rutiles, anatases and amorphous titanium dioxide having a particle size of 1 to 100 nm, preferably of 1 to 10 nm, or titanium dioxide having the above-stated particle size in dispersed form. A range of interesting industrial applications for such titanium dioxide particles is beginning to emerge:

as a UV screening agent in cosmetics, plastics, silicone resins and lacquers, wherein the transparency due to the small particle size is a particularly desirable characteristic of the particles;

as a flame retardant and to increase the refractive index of silicones and plastics, as described in FR 2 682 369;

in environmental protection to degrade organic pollutants, including halogenated pollutants, in waste waters by photocatalysis;

to accelerate the decomposition of (bio)degradable polymers;

as a support material for novel dye solar cells, as are described, for example, in PCT-WO 93/20569;

together with $SiO_2$ produced using the same method, as a component in special glasses.

The use of these $TiO_2$ nanoparticles is, however, currently still restricted by the fact that no economic process is known which is capable of producing nano-$TiO_2$ of the stated particle size on an industrial scale.

The most important methods for the synthesis of nanoparticles may be grouped together under the superordinate term of sol/gel processes. These processes have been described in many journal articles and patents.

The sol/gel process is more narrowly taken to mean the alkoxide method, i.e. the carefully controlled, frequently base- or acid-catalysed hydrolysis of metal alkoxides and similar molecular precursors in mixtures of water and one or more organic solvents. The solvent used is generally the same alcohol as the alkoxide is based upon. The disadvantage of this process is that costly educts and complicated processing are required. The products moreover have an elevated carbon content.

Originally developed for silicon compounds, the sol/gel process is increasingly also being used for the synthesis of nano-titanium dioxide in accordance with the equation

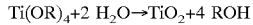

$$Ti(OR)_4 + 2 H_2O \rightarrow TiO_2 + 4 ROH$$

(c.f. for example J. Livage, *Mat. Sci. Forum* 152–153 (1994), 43–54; J. L. Look and C. F. Zukoski, *J. Am. Ceram. Soc.* 75 (1992), 1587–1595; WO 93/05875).

It is frequently possible to produce monodisperse particles, i.e. particles having a very narrow particle size distribution, by appropriate selection of the reaction conditions, wherein the diameter of the particles ranges from some micrometers down to a few nanometers. One example of such a special processing method is working in microemulsions, by which means it is possible to limit particle size (c.f for example D. Papoutsi et al., *Langmuir* 10 (1994), 1684–1689).

The educts for all sol/gel reactions for the production of nano-$TiO_2$, whether by conventional or microemulsion methods, are titanium alkoxides $Ti(OR)_4$, the alkyl residues R of which conventionally contain 2 to 4 carbon atoms. However, due to the high price of these alkoxides and particular handling requirements (protective gas, strict exclusion of moisture in order to prevent premature hydrolysis), the stated reactions cannot be considered for a large scale industrial process.

Working in microemulsions moreover has the disadvantage that, due to the frequently low concentration of the reactants, the space/time yield is low and that large quantities of water/solvent/surfactant mixtures are produced which much be disposed of.

An alternative, non-hydrolytic sol/gel process has recently been proposed (S. Acosta et al., *Better Ceramics through Chemistry* VI (1994), 43–54), which involves reacting metal halides with oxygen donors such as ethers or alkoxides.

Another group of methods for the production of ultra-fine titanium dioxide particles comprises the so-called CVR (chemical vapour reaction) processes, which are based upon the reaction of vaporisable metal compounds (generally alkoxides) with oxygen (air) or steam in the gas phase, as described, for example, in U.S. Pat. No. 4,842,832 and EP-A 214 308. While small quantities of powders produced using such processes are indeed already commercially available, they are extremely expensive.

Of the hitherto known processes performed on a large industrial scale for the production of finely divided (subpigmentary) titanium dioxide, namely hydrolysis of $TiCl_4$ (GB-A 2 205 288), production of rutile nuclei in the sulphate process (EP-A 444 798, EP-A 499 863) and peptisation with monobasic acids of titanium dioxide hydrate which has been washed free of sulphate EP-A 261 560, U.S. Pat. No. 2,448,683), none yields a product comparable in terms of fineness and transparency with sol/gel materials.

It is also known from the literature to hydrolyse $TiCl_4$ under hydrothermal conditions, wherein depending upon the reaction conditions (concentration, temperature, pH value, mineralisers), nano-anatases and nano-rutiles are obtained (H. Cheng et al., *Chem. Mater.* 7 (1995), 663–671). However, due to the complicated processing requirements, it is doubtful that a commercially viable product may be obtained using this method.

The object of the invention was thus to provide a nanodisperse titanium dioxide from which transparent sols may be produced, and to provide a process for the production thereof. The process for the production of nano-titanium dioxide should have the economic viability and relatively simple processing requirements of a large scale industrial process and the product of the process should have the favourable properties (fineness and transparency) of a sol/gel product.

The present invention provides a particulate nanodisperse titanium dioxide having a maximum value of the particle size distribution of between 1 and 10 nm determined by means of an ultracentrifuge containing less than 0.1 wt. % of carbon in the form of organic compounds or residues and having a transparency of at least 99% measured in a 5 wt. % aqueous/hydrochloric acid solution between 400 and 700 nm in 180°/d geometry at a layer thickness of 10 μm.

The titanium dioxide according to the invention may also be coated with 0.1 to 50 wt. %, preferably with 5 to 30 wt. %, relative to $TiO_2$, of at least one oxide, hydroxide or hydrous oxide compound of aluminium, silicon, zirconium, tin, magnesium, zinc, cerium and phosphorus.

The present invention also provides a transparent titanium dioxide sol containing a sol-forming medium and a sol-forming amount, not exceeding about 20 wt. % of the particulate nanodisperse titanium dioxide according to the invention, wherein said sol-forming medium preferably comprises water, an alcohol containing to 1 to 10 carbon atoms and at least one hydroxide group per molecule, or a mixture thereof.

The present invention furthermore provides a process for the production of the particulate nanodisperse titanium dioxide according to the invention, which comprises:

a) adding a solution comprising sulphuric acid and titanyl sulphate at elevated temperature to an alkaline-reacting liquid until the resultant mixture reacts acidically and forms titanium dioxide nanoparticles; or adding an alkaline-reacting liquid and a solution comprising sulphuric acid and titanyl sulphate simultaneously to a vessel, while mixing thoroughly at elevated temperature, until the resultant mixture reacts acidically and forms titanium dioxide nanoparticles;

b) cooling the mixture obtained in step a);

c) flocculating said titanium dioxide nanoparticles formed in step a) by adding a monobasic acid to the thus-cooled mixture obtained in step b);

d) filtering out the resulting titanium dioxide nanoparticle flocculate formed in step c); and e) washing said flocculate with a monobasic acid to obtain a precipitate.

The transparent titanium dioxide sol according to the invention is obtained by redissolving the precipitate obtained in step e) in a polar, sol-forming medium. The medium preferably comprises water, an alcohol containing 1 to 10 carbon atoms and at least one hydroxide group per molecule, or a mixture thereof.

The nanodisperse $TiO_2$ according to the invention may surprisingly also successfully be produced within a large scale industrial process, namely $TiO_2$ pigment production using the sulphate process, and is thus very simple and economically viable.

The filter residue obtained (after step d)) using the process according to the invention may be inorganically and/or organically post-treated.

In principle, any titanyl sulphate solution containing sulphuric acid in excess is suitable as the educt (sulphuric-acid titanyl sulphate solution). Contamination by metals which form soluble sulphates and chlorides, such as for example iron, magnesium, aluminium and alkali metals do not in principle disrupt the production process, unless the stated elements have a disadvantageous effect even in trace quantities in the intended application. It is thus possible to perform the process according to the invention on a large industrial scale. Black liquor, as is obtained from the sulphate process by digesting ilmenite and/or titanium slag with sulphuric acid, dissolving the resultant digestion cake in water and performing clarification, may for example be used as the educt.

The production process according to the invention is, however, not restricted to black liquor as the educt. Examples of other processes for the production of a sulphuric-acid titanyl sulphate solution suitable as an educt are:

a) dissolution/digestion of titanium dioxide and $TiO_2$ hydrates, for example orthotitanic acid, metatitanic acid, in excess $H_2SO_4$;

b) dissolution/digestion of alkali metal and magnesium titanates, also in hydrous form, in excess $H_2SO_4$;

c) reaction of $TiCl_4$ with excess $H_2SO_4$ to form $TiOSO_4$ and HCl, as described in DE-A 4 216 122.

The products, in particular those from a) and c), are preferably used as sulphuric-acid titanyl sulphate solutions when traces of foreign metals (for example iron) are not desired in the product according to the invention.

In order to achieve economically viable operation, the sulphuric-acid titanyl sulphate solutions to be used according to the invention preferably contain 100 to 260, particularly preferably 170 to 230 g of titanium/l, calculated as $TiO_2$. The acid excess preferably amounts to 0.3 to 4.0, particularly preferably to 0.5 to 1.5 mol of $H_2SO_4$ per mol of $TiOSO_4$.

Aqueous solutions of sodium hydroxide, potassium hydroxide or ammonia are preferably used as the alkaline-reacting liquids; it is, in principle, also possible to use carbonates of sodium, potassium and ammonium, but these are less suitable due to vigorous evolution of $CO_2$. Sodium hydroxide solution is particularly preferred and is used to illustrate performance of the process in greater detail.

The quantity of sodium hydroxide should e.g. be calculated such that the sodium hydroxide is present in a stoichiometric deficit relative, for example, to the "free sulphuric acid", after step a). For the purposes of the sulphate process for the production of $TiO_2$, the person skilled in the art understands "free sulphuric acid" to mean the total sulphur content minus that proportion bound in the form of foreign metal sulphates (primarily $FeSO_4$), i.e. the sum of the $H_2SO_4$ and the sulphuric acid bound as $TiOSO_4$, this latter proportion being present as $H_2SO_4$ after hydrolysis.

The quantity of sodium hydroxide is adjusted to a stoichiometric deficit with regard to the two reactions

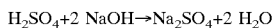

$$H_2SO_4 + 2\ NaOH \rightarrow Na_2SO_4 + 2\ H_2O$$

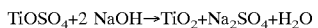

$$TiOSO_4 + 2\ NaOH \rightarrow TiO_2 + Na_2SO_4 + H_2O$$

wherein the deficit is preferably selected such that the pH value is preferably less than 2 at the end of step a).

The sodium hydroxide is preferably used as a sodium hydroxide solution having a concentration of preferably approximately 5 to 10 wt. % of NaOH.

The reaction of the sub-stoichiometric sodium hydroxide solution with the sulphuric-acid titanyl sulphate solution preferably proceeds in such a manner that the sodium hydroxide, heated to approximately 60° to 100° C., is initially introduced into a vessel and the sulphuric-acid titanyl sulphate solution is run into this solution.

Preferably the reaction in step a) can also be carried out by adding the two reactants simultaneously and mixing them with stirring at temperatures of between 60° and 100° C.

Step a) should preferably be performed with vigorous stirring and at temperatures of 60° to 100° C.

The pH of the initial amount should pass through and leave the alkaline range as quickly as possible (preferably in less than 5 minutes).

After step a), the mixture should preferably be quenched to temperatures of below 60° C. and then optionally stirred for ½ to 2 hours at this temperature.

The resultant mixture is turbid to a greater or lesser extent (turbid sol). Such mixtures are used as so-called hydrolysis nuclei in the $TiO_2$ sulphate process. They are not suitable as transparent sols.

After cooling, the mixture is flocculated with a monobasic acid and the flocculate isolated by filtration. The flocculate is nanodisperse titanium dioxide having a particle size of between 1 and 10 nm, containing less than 0.1 wt. % of carbon and having a transparency of at least 99% (see above).

The mixture is preferably clarified before the monobasic acid is added. This may be performed simply by settling, i.e.

standing undisturbed for at least 12 hours and decantation. It is, however, also possible to centrifuge or filter the mixture, if necessary with a filter aid.

The addition of the monobasic mineral acid reversibly flocculates the nanoparticles formed in step a). Due to their size (preferably 1 to 10 μm), the resultant bulky flocs may readily be centrifuged and filtered. The preferred monobasic acid is hydrochloric acid, which is used to illustrate the further processing in greater detail. The same procedure should be used with other monobasic mineral acids.

The HCl concentration in the hydrochloric acid should preferably be no less than 1 molar, concentration is preferably adjusted to 1 to 6 molar, particularly preferably to 1 to 4 molar.

Preferred filter cloths are those made from acid-resistant material (for example polypropylene). Particularly suitable are those acid-resistant filter cloths known to the person skilled in the art which are used to isolate $TiO_2$ hydrolysate in the sulphate process, as well as membrane filters based on cellulose, cellulose ethers or cellulose esters.

The precipitate is then washed, preferably with the same monobasic acid as was used for flocculation. In the case of hydrochloric acid, 3 to 6 molar hydrochloric acid is particularly suitable as washing liquid.

Depending upon the filter unit and starting material, the resultant (salt-)acid precipitates (pastes) contain 20 to 40, typically approximately 30 wt. % of $TiO_2$, the remainder being wash acid and possibly small quantities of contaminants.

Once redissolved in water, the precipitates yield "solutions" (sols) which, apart from slight opalescence (Tyndall effect), are clear, transparent and colourless or nearly colourless. The $TiO_2$ is present in these sols exclusively as nanoparticles having a diameter of between 1 and 10 nm.

It is possible in this manner to produce strongly acidic, virtually completely transparent (water-clear) sols containing up to approximately 20 wt. % of $TiO_2$. At a concentration of 5 wt. % of $TiO_2$, the transparency of the sols is above 99% over the entire visible range of the spectrum (measured in 180°/d geometry).

The nanoparticles may be reflocculated by adding monobasic mineral acids, for example HCl, filtered and washed. In this form, they may be stored at around 0° C. without change for some weeks.

Similar sols may also be produced in polar organic solvents, primarily in mono- and polyhydric short-chain alcohols, such as for example ethanol and 1,4-butanediol. The alcohols preferably contain 1 to 10 carbon atoms per molecule.

The pastes may be converted into glassy xerogels by vaporising the liquid and adhering acid at the lowest possible temperature under a vacuum or over NaOH (room temperature, freeze drying), which xerogels may be converted into clear aqueous dispersions unless too much $H_2O$ and HCl have been separated.

Any heavy metal ions possibly present may be depleted by dialysis against dilute monobasic mineral acids.

When the hydrochloric-acid sol is dialysed against distilled water, condensation of the nanoparticles results in the formation of gels which, if the $TiO_2$ concentration is sufficiently high, may be monolithic.

In applications in which acid excesses have a disruptive effect, the particles according to the invention may subsequently be stabilised in the neutral pH range in a manner known in principle, for example with acetylacetone (WO 93/05875) or with hydroxycarboxylic acids (EP-A 518 175).

The nanodisperse titanium dioxide is used as a UV screening component in cosmetics, plastics, silicone resins and lacquers.

In the event that a reduction in photoactivity is desired, the nanoparticles may be inorganically coated (post-treated), wherein, as with pigment $TiO_2$, coating is performed with oxides, hydroxides or hydrous oxides of one or more of the following elements: Al, Si, Zr, Sn, Mg, Zn, Ce, P. The quantities to be used amount to 0.1 to 50, preferably to 5 to 30 wt. %, relative to $TiO_2$.

Inorganic post-treatment is not necessary, and is indeed undesirable, if the product is used as a catalyst for the photochemical degradation of organic compounds (polymers, pollutants) or as a support for dye solar cells.

BRIEF DESCRIPTION OF THE DRAWINGS

FIG. 1 is a graph showing the transmittance of an aqueous $TiO_2$ sol according to the invention and of a prior art $TiO_2$ sol.

FIG. 2 is a graph showing the particle size distribution of nanodisperse titanium dioxide according to the invention as determined by ultracentrifugation.

The following examples are intended to illustrate the invention in greater detail.

EXAMPLES

Example 1 (production of nano-$TiO_2$ from so-called black liquor)

1400 ml of 7.5 wt. % aqueous sodium hydroxide solution are heated to 85° C. in a double-walled, heatable, 6 liter flat-ground glass vessel with a mechanical stirrer, thermometer, reflux condenser and a bottom valve to discharge the product. 804 ml of black liquor containing $FeSO_4$ produced using the sulphate process ($d_{60°}$ C.1.566 g/ml; 13.83 wt. % $TiO_2$ corresponding to 217 g/l; 28.39 wt. % free $H_2SO_4$) are heated to 60° C. in a 1 liter 3-necked flask with stirrer, reflux condenser, heating mantle and bottom outlet valve. The black liquor is run through a glass nozzle within a full 3 minutes into the initial amount of sodium hydroxide solution with vigorous stirring, wherein a dense, dark precipitate is temporarily formed. The temperature of the mixture rises to 92° C. due to the heat of neutralisation. After stirring for approximately a further 5 minutes, the mixture is only slightly turbid. The mixture is then cooled to 30° C. in 20 minutes with further stirring.

244 ml of semi-concentrated hydrochloric acid (20.6 wt. %, approximately 6.2 molar) is added dropwise within 5 minutes to 244 ml of a mixture produced in this manner. A white precipitate is formed. After standing for 1 hour to complete the precipitation, the precipitate is suction-filtered by means of a cellulose nitrate filter and washed with a total of 900 ml of the above-stated hydrochloric acid in portions.

32.5 g of a white paste are obtained which contains 34.5 wt. % of $TiO_2$ (corresponding to 58% of theoretical), 14.7 wt. % of HCl, 2.7 wt. % of $SO_4^{2-}$ and 170 ppm of Fe.

10.8 g of the paste are dissolved in 32.1 g of distilled water. The "solution" contains approximately 8.3 wt. % of $TiO_2$ and 3.6 wt. % of HCl and is virtually clear.

Example 2 (Production of nano-$TiO_2$ from $TiOSO_4$ solution)

The same method was used as in Example 1. However, instead of the black liquor, the titanium educt used was a titanyl sulphate solution (804 ml; d=1.272 g/ml; 8.2 wt. % $TiO_2$, 23.5 wt. % $H_2SO_4$) obtained by dissolving sodium titanate in sulphuric acid. As in Example 1, the initial amount contains 1400 ml of 7.5 wt. % NaOH, and the feed time of the titanyl sulphate solution is 4 minutes. After cooling to room temperature, a white suspension is obtained.

400 ml of this suspension are combined within 10 minutes with 400 ml of semi-concentrated hydrochloric acid. After standing for 1 hour to complete the precipitation, the precipitate is suction-filtered by means of a cellulose nitrate filter and washed with a total of 1700 ml of the above-stated hydrochloric acid in portions.

The filter cake is suction-dried for a further 22 h at room temperature, wherein a yellowish, glassy xerogel (15.6 g) containing 59.8 wt. % of $TiO_2$ (corresponding to 65% of theoretical), 9.8 wt. % of HCl and 1.23% of sulphate is obtained.

5 g of the xerogel are dissolved in 20 g of distilled water. The resultant sol is transparent, apart from slight opalescence, and contains approximately 11.8 wt. % of $TiO_2$ and 1.94 wt. % of HCl.

Example 3 (Production of a $TiO_2$ gel by dialysis)

41.5 g of a paste obtained according to Example 1 are mixed with 46 g of the above-stated hydrochloric acid to yield a suspension containing 10.8 wt. % of $TiO_2$, 18.1 wt. % of HCl and 0.92 wt. % of $SO_4^{2-}$. 34.2 g of this mixture are dialysed against distilled water in a cellophane tube for 3.5 hours, wherein the initially turbid suspension becomes a transparent sol. After dialysis, the sol (39.9 g) contains 8.9 wt. % of $TiO_2$, 0.85 wt. % of HCl and 0.89 wt. % of $SO_4^{2-}$.

After storage for 24 hours at room temperature, a great increase in viscosity is observed and, after a total of 48 hours' storage, the sol has become a non-flowing, monolithic, transparent, cuttable gel.

Comparative Example 1 (Prior art production of a $TiO_2$ sol: U.S. Pat. No. 2,448,683)

620 g of a purified titanium dioxide hydrate slurry from the sulphate process containing approximately 19.5 wt. % of $TiO_2$ (121 g) and approximately 7 wt. % of $H_2SO_4$ relative to $TiO_2$ are neutralised to pH 7.1 at room temperature with 50 wt. % sodium hydroxide solution. After filtration, the filter cake is washed with approximately 3 liters of distilled water until the filtrate gives a negative result in the $BaSO_4$ test. 400 g of the filter cake containing approximately 28 wt. % of $TiO_2$ and approximately 0.3 wt. % of $SO_4^{2-}$ relative to $TiO_2$ are combined with 5 wt. % of HCl (relative to $TiO_2$) in the form of concentrated hydrochloric acid and sufficient water to produce a mixture containing 25 wt. % of $TiO_2$. After 30 minutes' stirring at room temperature, a low viscosity, white sol is obtained.

When diluted with water to 5 to 10 wt. % of $TiO_2$, the sol remains white and milky, unlike the virtually water-clear sols obtained according to Examples 1 and 2. Even if the HCl concentration is increased, the sol does not become transparent.

Transmission measurements

A specimen of the paste obtained according to Example 1 is adjusted to a concentration of 5 wt. % of $TiO_2$ and 2.5 wt. % of HCl with semi-concentrated hydrochloric acid and distilled water. The sol obtained according to Comparative Example 1 is diluted to 5 wt. % of $TiO_2$ with distilled water. (It is not possible to adjust the HCl concentration to 2.5 wt. % due to flocculation phenomena).

UV-VIS spectra are measured at a layer thickness of 10 $\mu$m in 180°/d geometry and are reproduced in FIG. 1.

The Figure shows that both specimens exhibit elevated absorption in the ultra-violet range of the spectrum, while the nano-$TiO_2$ according to the invention (specimen A) is, however, substantially more transparent in the visible range of the spectrum (400 to 700 nm) than the prior art sol (specimen B). Moreover, the inflection point of the steep absorption edge is shifted down to a shorter wavelength in comparison with the comparison sol.

Particle size measurement

The particle size distribution of a specimen of paste obtained as in Example 1 is determined by means of an ultracentrifuge (solvent: water/HCl). According to this determination, the average diameter is approximately 4.5 nm. The distribution is shown in FIG. 2.

Using the same equipment, an average diameter of 36 nm is determined for the comparison sol from Comparative Example 1.

Weathering test on un-post-treated nano-$TiO_2$ in ABS

Two specimens of an acrylonitrile/butadiene/styrene copolymer, one of which contains 5 wt. % of the nano-$TiO_2$ according to the invention and one is untreated, are weathered (to DIN 53387 (1989)) in a xenon Weatherometer with an irradiation intensity of 0.35 W/m². The spraying cycle is 102 min (dry): 18 min (spraying with distilled water). Gloss (to DIN 67530 (1982)) at an angle of 60° is measured as a function of the duration of weathering with a Dataflash 2000 colorimeter (ASTM D 1925). In this test arrangement, polymer degradation on the specimen surface results in a reduction in gloss. The results are summarised in the following table.

| Weathering time (hours) | ABS with 5% nano-$TiO_2$ Gloss | ABS without $TiO_2$ Gloss |
| --- | --- | --- |
| 0 | 86 | 92 |
| 250 | 4 | 88 |
| 500 | 3 | 86 |
| 1000 | 3 | 52 |

The values from the table show that the nanodisperse titanium dioxide very strongly accelerates the reduction in gloss and thus degradation of the polymer or, in general terms, of organic materials.

What is claimed is:

1. A particulate nanodisperse titanium dioxide having a maximum particle size distribution of between 1 and 10 nm, determined by means of an ultracentrifuge, containing less than 0.1 wt. % of carbon in the form of organic compounds or residues, and having a transparency of at least 99% measured in a 5 wt. % aqueous/hydrochloric acid solution between 400 and 700 nm in 180°/d geometry at a layer thickness of 10 $\mu$m.

2. The particulate nanodisperse titanium dioxide as claimed in claim 1, wherein the titanium dioxide is coated with 0.1 to 50 wt. %, relative to $TiO_2$, of at least one oxide, hydroxide or hydrous oxide compound of aluminum, silicon, zirconium, tin, magnesium, zinc, cerium, or phosphorous or a mixture of said compounds.

3. A transparent titanium dioxide sol containing a sol-forming medium and less than about 20 wt. % of the particulate nanodisperse titanium dioxide as claimed in claim 1.

4. A process for producing a particulate nanodisperse titanium dioxide having a maximum particle size distribution of between 1 and 10 nm, determined by means of an ultracentrifuge, containing less than 0.1 wt. % of carbon in the form of organic compounds or residues, and having a transparency of at least 99% measured in a 5 wt. % aqueous/hydrochloric acid solution between 400 and 700 nm in 180°/d geometry at a layer thickness of 10 $\mu$m, which process comprises the following steps:

a) mixing a solution comprising sulphuric-acid and titanyl sulphate at an elevated temperature and an alkaline-reacting liquid until the mixture reacts acidically and forms titanium dioxide nanoparticles; or adding an alkaline-reacting liquid and a solution comprising sulphuric acid and titanyl sulphate simultaneously to a vessel, while mixing thoroughly at the elevated temperature, until the resultant mixture reacts acidically and forms titanium dioxide nanoparticles;

b) cooling the mixture obtained in step a);

c) flocculating the titanium dioxide nanoparticles formed in step a) by adding a monobasic acid to the thus-cooled mixture obtained in step b);

d) filtering out the resulting titanium dioxide nanoparticle flocculate formed in step c); and e) washing the flocculate with a monobasic acid to obtain a precipitate.

5. The process as claimed in claim 4, further comprising: redissolving the precipitate obtained according to step e), in a polar, sol-forming medium.

6. The process as claimed in claim 4, wherein the solution comprises black liquor.

7. The process as claimed in claim 4, wherein said solution is obtained by dissolving titanium dioxide, a titanium dioxide hydrate, a titanate or a titanium halide in sulphuric acid, and the sulphuric-acid titanyl sulphate solution contains 100 to 260 g/l of, titanium, calculated as $TiO_2$ and, in addition to the proportion bound as titanyl sulphate, 0.3 to 4 mol of sulphuric acid per mol of $TiOSO_4$.

8. The process as claimed in claim 7, wherein said solution contains 170 to 230 g/L of titanium, calculated as $TiO_2$ and, in addition to the proportion bound as titanyl sulphate, 0.5 to 1.5 mole of $H_2SO_4$ per mol of $TiOSO_4$.

9. The process as claimed in claim 4, wherein the alkaline-reacting liquid is an aqueous solution of sodium hydroxide, potassium hydroxide or ammonia or a mixture thereof.

10. The process as claimed in claim 4, wherein the alkaline-reacting liquid is an aqueous solution comprising sodium hydroxide having a concentration of approximately 5 to 10 wt. % of NaOH.

11. The process as claimed in claim 4, wherein the sulphuric-acid titanyl sulphate solution is black liquor sulphate and the alkaline-reacting liquid is sodium hydroxide solution.

12. The process as claimed in claim 4, wherein step a) is performed at a temperature between 60° and 100° C.

13. The process as claimed in claim 4, wherein, after reaction step a), the mixture has a pH of less than 2.

14. The process as claimed in claim 4, wherein the mixture obtained in step a) or step b) is clarified by settling, filtration or centrifugation before it is subjected to step b) or c).

15. The process as claimed in claim 4, wherein the monobasic acid comprises hydrochloric acid.

16. The process as claimed in claim 4, wherein the precipitate e) is redissolved in an aqueous medium or an alcohol which contains 1 to 10 carbon atoms and one or more hydroxide groups or a mixture thereof to obtain a transparent titanium dioxide sol.

17. A method for absorbing ultraviolet radiation in a cosmetic, which comprises the step of introducing into said cosmetic a nanodisperse titanium dioxide according to claim 1.

18. A dye solar cell comprising, as a support material, a nanodisperse titanium dioxide as claimed in claim 1.

19. A transparent titanium dioxide sol as claimed in claim 3, wherein said sol-forming medium comprises a combination of water and an alcohol having at least one hydroxide group per molecule.

20. A transparent titanium dioxide sol as claimed in claim 3, wherein said sol-forming medium is an organic polar solvent.

21. A transparent titanium dioxide sol as claimed in claim 20, wherein said sol-forming medium is a mono- or polyhydric alcohol having 1 to 10 carbon atoms.

22. A method for degrading an organic pollutant or a biodegradable polymer, which method comprises the step of introducing a particulate nanodisperse titanium dioxide into waste water containing the pollutant or the polymer, wherein the particulate nanodisperse titanium dioxide has a maximum particle size distribution of between 1 and 10 nm, determined by means of an ultracentrifuge, contains less than 0.1 wt. % of carbon in the form of organic compounds or residues, and has a transparency of at least 99% measured in a 5 wt. % aqueous/hydrochloric acid solution between 400 and 700 nm in 180°/d geometry at a layer thickness of 10 $\mu$m.

23. A particulate nanodisperse titanium dioxide having a maximum particle size distribution of between 1 and 4.5 nm, determined by means of an ultracentrifuge, containing less than 0.1 wt. % of carbon in the form of organic compounds or residues, and having a transparency of at least 99%, measured on a 5 wt. % aqueous/hydrochloric acid solution between 400 and 700 nm in 180°/d geometry at a layer thickness of 10 $\mu$m.

24. A particulate nanodisperse titanium dioxide having a maximum particle size distribution of between 1 and 10 nm, determined by means of an ultracentrifuge, containing less than 0.1 wt. % of carbon in the form of organic compounds or residues, and having a transparency of at least 99%, measured on a 5 wt. % aqueous/hydrochloric acid solution between 400 and 700 nm in 180°/d geometry at a layer thickness of 10 $\mu$m, wherein the particulate nanodisperse titanium dioxide consists essentially of titanium dioxide and at least one metal contaminant, the at least one metal contaminant being iron, magnesium, aluminum, or an alkali metal.

25. The particulate nanodisperse titanium dioxide as claimed in claim 24, wherein the particle size distribution is between 1 and 4.5 nm.

* * * * *